United States Patent

McQuilkin

Patent Number: 5,193,554
Date of Patent: Mar. 16, 1993

[54] STERILIZATION DEVICES

[75] Inventor: Peter H. McQuilkin, Kimberley, England

[73] Assignee: Femcare Limited, Nottingham, United Kingdom

[21] Appl. No.: 699,482

[22] Filed: May 13, 1991

[30] Foreign Application Priority Data

May 12, 1990 [GB] United Kingdom ............... 9010696

[51] Int. Cl.⁵ .............................................. A61B 17/12
[52] U.S. Cl. .................................... 128/831; 128/830; 606/120
[58] Field of Search ............... 128/831, 843; 606/120, 606/135, 136, 151, 157, 158

[56] References Cited

U.S. PATENT DOCUMENTS

| 3,854,482 | 12/1974 | Laugherty et al. | 606/120 |
| 3,926,195 | 12/1975 | Bleier et al. | 606/135 X |
| 4,489,725 | 12/1984 | Casey et al. | 606/135 X |
| 5,002,552 | 3/1991 | Casey et al. | 606/135 X |

FOREIGN PATENT DOCUMENTS

| 24687 | 11/1987 | European Pat. Off. | 128/831 |
| 1530282 | 10/1978 | United Kingdom | 128/831 |
| 2190297 | 11/1987 | United Kingdom | 128/831 |

Primary Examiner—Robert A. Hafer
Assistant Examiner—Sam Rimell
Attorney, Agent, or Firm—Salter, Michaelson & Benson

[57] ABSTRACT

A sexual sterilization clip comprises an upper and lower jaw of plastics material with capture means for capturing the fallopian tube or vas deferens the capture means being provided with a soft lining.

3 Claims, 2 Drawing Sheets

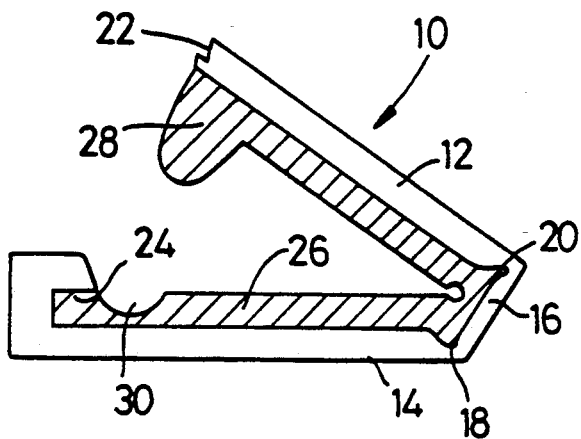
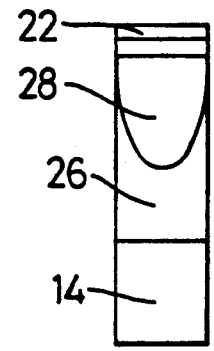
Fig. 1  Fig. 2
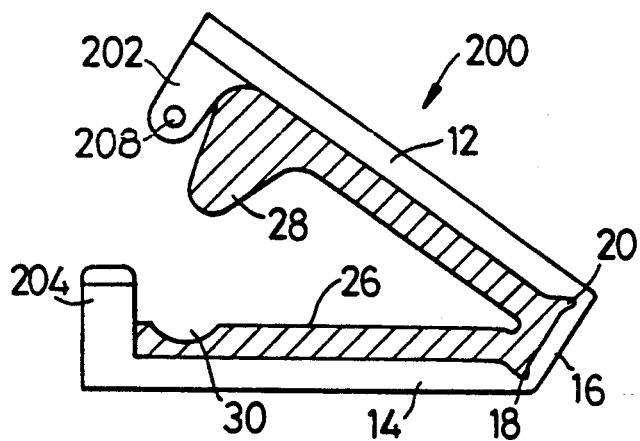
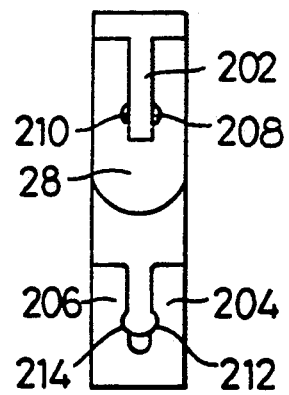
Fig. 3  Fig. 4

STERILIZATION DEVICES

The present invention relates to sexual sterilisation devices and more particularly to sexual sterilisation clips adapted to be clamped on a fallopian tube or a vas deferens to effect occlusion thereof.

It is an object of the present invention to provide sterilisation clips which may be manufactured with a frame constructed from plastics material.

The present invention provides a sexual sterilisation clip having a lower jaw member and an upper jaw member hingedly connected at one end to the lower jaw member, the upper and lower jaw members being provided, at an opposite end thereof in relation to the hinge, with co-operating latch means to secure the clip in a closed position, the clip being provided in an open position with projection means to provide initial capture of a fallopian tube or vas deferens.

Preferably the projection means in a first embodiment comprises a profiled inner top lining for the upper jaw.

Preferably the linings are made of silicone rubber.

Embodiments of the present invention will now be described, by way of example with reference to the accompanying drawings, in which:

FIG. 1 shows in side elevation a clip illustrating a first embodiment of the present invention;

FIG. 2 shows the first clip in end elevation;

FIG. 3 shows a clip in side elevation illustrating a third embodiment of the present invention;

FIG. 4 shows the clip of FIG. 3 in end elevation; and

Figure 5:
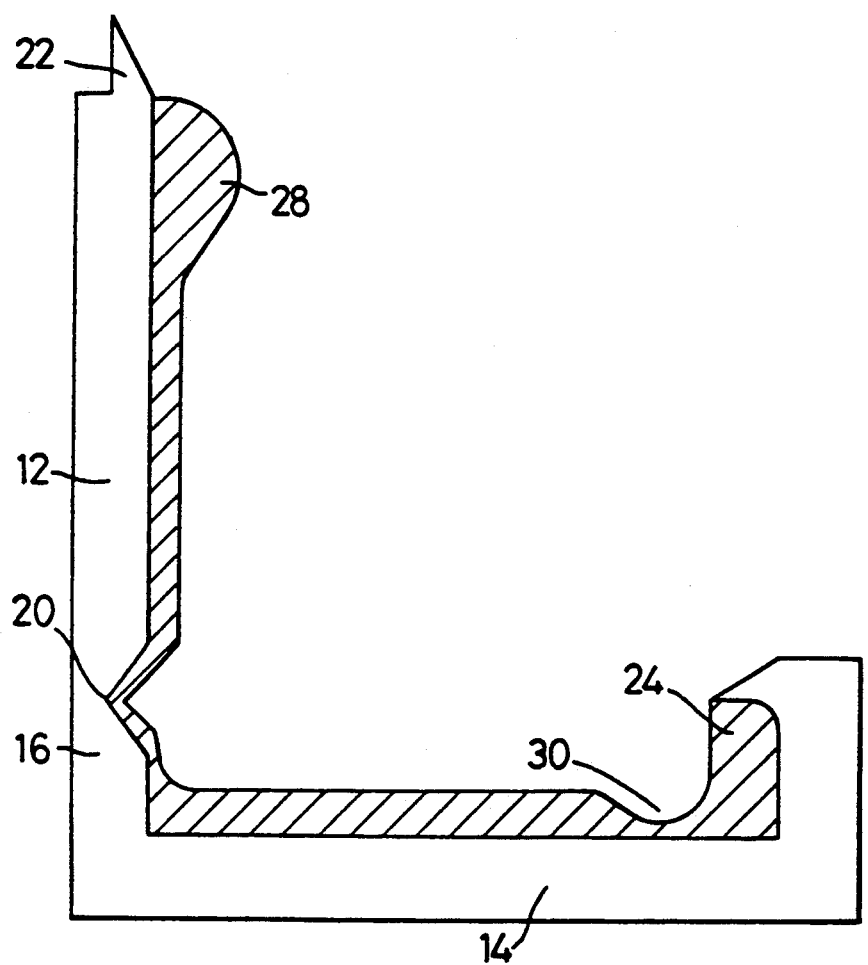
FIG. 5 shows an alternative clip.

With reference now to FIG. 1 the clip 10 comprises an upper jaw 12 and a lower jaw 14 hingedly connected at one end by a slightly thinner section 16 moulded integrally with the upper and lower jaws and relieved at the corners 18, 20 to allow closure of the clip.

Closure of clip 10 is effected by squeezing the two jaw members together and latching is effected by co-operating detente 22 and a recessed portion 24 on the lower jaw. Once latched the clip cannot be opened without substantial force.

The internal surfaces of upper and lower jaws 12, 14 are lined with a soft lining 26, preferably of silicone rubber, which may be formed in one piece as shown or may be in two pieces joined at an appropriate position near the hinge 16.

The lining on the upper jaw member is provided with a top profile 28 which is enlarged to form a bulge at the latch end of the clip.

The lining on the lower jaw 14 is preferably provided with a profile which is relieved at 30 to permit the top bulge 28 to access without excessive closing pressure being required for the clip.

The profile 28 serves to capture the fallopian tube as the clip closes but prior to final closure of the clip thereby preventing the tube from escaping from the clip as the final.

The flexible action 112 provides a means for capturing the fallopian tube during initial closure of the clip but prior to final closure pressure being applied. The lining 114 is continuous around the inside of the lower jaw 104 and section 112 and therefore complete occlusion of the fallopian tube is effected.

By suitable design of the detent 22 of the design of FIGS. 1 and 2 and the recessed portion 24 the clip when closed will present a substantially completely flat top, this feature being advantageous.

With reference now to FIGS. 3 and 4 an alternative embodiment of the clip shown in FIGS. 1 and 2 is shown. In FIGS. 3 and 4 those parts performing the same or equivalent functions are given the same reference numerals.

The alternative clip 200 comprises upper and lower jaw members 12, 14 silicone lining 26 with profiles 28, 30 and is hinged 16, 18, 20 as in FIGS. 1 and 2. The latch means however comprises interdigitating fingers 202 (upper jaw) and 204, 206 (lower jaw). Finger 202 is provided with a broadened portion 208, 210 which co-operates with two recessed portions 212, 214 on respective fingers 204, 206 to provide positive latching for the clip.

This type of latching is particularly advantageous for the clip of FIGS. 1 and 2 since the finger 202 provides a support for profile 28.

The hinge for the clips may be of the type shown in FIG. 1. The hinge in FIG. 1 has the advantage that the clip is of one piece manufacture.

The type of latching shown in FIG. 3 can be used with the clip design of FIG. 2.

With reference now to FIG. 7, an alternative clip design is shown which is similar to the design of FIGS. 1 and 2.

The reference numerals of FIGS. 1 and 2 are used to identify parts performing similar functions. The practical dimensions (in mm) of the clip of FIG. 7 are as follows:

L1: 12.25
L2: 1.54
L3: 2.06
L4: 4.67
L5: 14.00
L6: 2.75
L7: 1.59
L8: 0.71
L9: 1.59
L10: 5.06

I claim:

1. A sexual sterilisation clip having a lower jaw member and an upper jaw member hingedly connected at one end to the lower jaw member, both jaw members being of plastics material, the upper and lower jaw members being provided, at an opposite end thereof in relation to the hinge, with co-operating latch means to secure the clip in a closed position, the clip being provided in an open position with projection means to provide initial capture of a fallopian tube or vas deferens in which both the upper and lower jaw members are provided with a rubber lining, in which the rubber lining of the upper jaw is shaped to provide a bulge at the latch means end of the upper jaw, said bulge being formed by an area of increased thickness in the rubber lining of the upper jaw and projecting towards the bottom jaw and in which the rubber lining of the lower jaw is provided with a recessed area of reduced thickness at the latch means end of the lower jaw which is aligned with the bulge and co-operates therewith as the clip is closed to provide an area of initial contact between the lining of the upper jaw and the lining of the lower jaw without significantly increasing the compression forces required to close the clip.

2. A sterilisation clip as claimed in claim 1 in which the co-operating latch means comprises a detent on the upper jaw and a co-operating recessed portion on the lower jaw.

3. A sterilisation clip as claimed in claim 1 in which the co-operating latch means comprises co-operating interdigitating fingers provided respectively at the ends of the upper and lower jaws one of the fingers on one of the jaws being provided with a broadened portion which co-operates with a recessed portion on one of the fingers on the other jaw to provide a positive snap action latch for the clip.

* * * * *

UNITED STATES PATENT AND TRADEMARK OFFICE
CERTIFICATE OF CORRECTION

PATENT NO. : 5,193,554  
DATED : March 16, 1993  
INVENTOR(S) : McQuilkin, Peter H.

Page 1 of 2

It is certified that error appears in the above-indentified patent and that said Letters Patent is hereby corrected as shown below:

Column 2, lines 23 and 28, change "Fig. 7" to --Fig. 5--; and substitute new Fig. 5 for Fig. 5 as issued, as shown on attached page.

Signed and Sealed this

Twenty-ninth Day of March, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,193,554                                    Page 2 of 2
DATED     : Mar. 16, 1993
INVENTOR(S) : McQuilkin, Peter H.

It is certified that error appears in the above-identified patent and that said Letters Patent is hereby corrected as shown below:

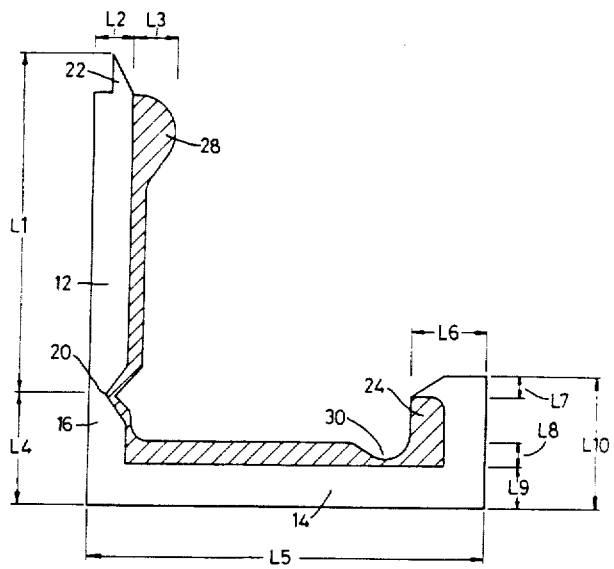

Fig. 5